(12) United States Patent
Thayer, II

(10) Patent No.: US 6,426,432 B1
(45) Date of Patent: Jul. 30, 2002

(54) ONE STEP PROCESS FOR PRODUCING DICARBOXYLIC ACIDS

(75) Inventor: Chester Arthur Thayer, II, Wilmington, DE (US)

(73) Assignee: E. I. DuPont de Nemours & Company, Wilmington, DE (US)

(*) Notice: Subject to any disclaimer, the term of this patent is extended or adjusted under 35 U.S.C. 154(b) by 0 days.

(21) Appl. No.: 09/949,567

(22) Filed: Sep. 10, 2001

(51) Int. Cl.[7] .................................................. C07C 55/00
(52) U.S. Cl. ..................................... 562/512.4; 562/590
(58) Field of Search ............................... 562/512.4, 590

(56) References Cited

U.S. PATENT DOCUMENTS 3,280,183 A  10/1966  Maggiolo
3,979,450 A * 9/1976  Moskovich et al. ...... 260/537 P
4,287,130 A * 9/1981  Dohm et al. .................. 260/413
4,940,808 A * 7/1990  Schulz et al. ................ 549/436

OTHER PUBLICATIONS

Bailey, Philip S., "Ozonation in Organic Chemistry," pp. 302–307, Academic Press, NY, 1982.

* cited by examiner

Primary Examiner—Paul J. Killos
Assistant Examiner—Zachary C. Tucker

(57) ABSTRACT

A process for making an alkanedioic acid in which a mixture of a cycloalkene, a base and a solvent is contacted simultaneously with both oxygen and ozone at a temperature between 40 and 60 degrees Centigrade.

9 Claims, 1 Drawing Sheet

ONE STEP PROCESS FOR PRODUCING DICARBOXYLIC ACIDS

FIELD OF THE INVENTION

This invention relates to a process for making dicarboxylic acids in which a cycloalkene is ozonized to produce an ozonide, the ozonide is converted to an acid aldehyde in the presence of heat and a base, and the acid aldehyde is oxidized to produce the desired dicarboxylic acid.

BACKGROUND OF THE INVENTION

It is known that ozonolysis of cyclododecene is a way of making dodecanedioic acid. See, for example, U.S. Pat. 3,280,183. The use of ozone as an oxidant and as an initiator for autoxidation also is known. (See Philip S. Bailey, "Ozonation in Organic Chemistry", pp. 302–307. Academic Press, New York, 1982.)

It is known in the art that a cycloalkene can be converted to a dicarboxylic acid using three separate, sequential reaction steps, conducted under different conditions. The first step, ozonolysis, involves contacting the cycloalkene with ozone at a low temperature, typically 20° C. or less. The ozonide so formed is then re-arranged with or without a base catalyst at a higher temperature, typically 80 to 100° C., to form an acid aldehyde. The acid aldehyde is then air oxidized at 80 to 100° C. to form the desired dicarboxylic acid product.

BRIEF SUMMARY OF THE INVENTION

The present invention is a process for making an alkanedioc acid, in which the alkane moiety contains 6 to 12 carbon atoms, comprising, forming a reaction mixture comprising a cycloalkene having the same number of carbon atoms as the alkane moiety of the alkanedioc acid, a $C_1$ to $C_9$ organic acid solvent, and a base catalyst, which is a metal salt of the organic acid, and contacting the mixture simultaneously with oxygen and ozone at a temperature between about 40 to about 60 degrees C. to obtain a product mixture comprising the alkanedioic acid.

BRIEF DESCRIPTION OF THE DRAWING

The drawing consists of one FIGURE showing a block diagram of apparatus that can be used to practice the present invention.

DETAILED DESCRIPTION OF THE INVENTION

Figure 1:
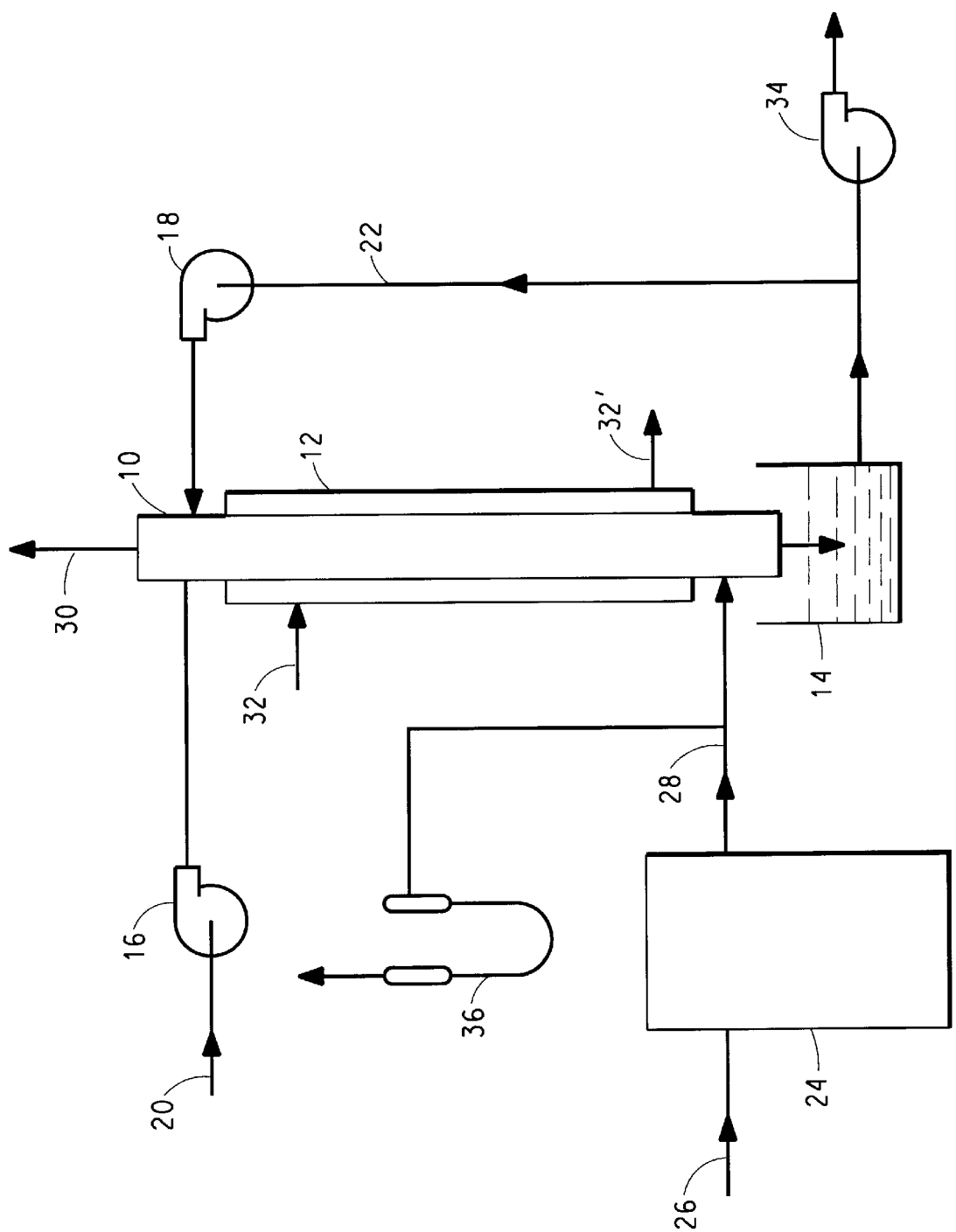

In the present invention, all three reaction steps of the prior art (ozonolysis of the cycloalkene to produce an ozonide, rearrangement of the ozonide to produce an acid aldehyde, and oxidation of the acid aldehyde to produce a dicarboxylic acid), are carried out at a temperature of 40 to 60° C., using both oxygen and ozone. Although ozonolysis within this temperature range leads to certain disadvantages, namely byproduct reactions and loss in yield, these disadvantages are offset by two beneficial phenomena that are believed to occur. First, the rearrangement of the ozonide to the acid aldehyde is believed to proceed rapidly in the presence of the base catalyst. Second, there is believed to be a significant increase in autoxidation when both oxygen and ozone are available. The net result is that the present invention provides a process in which all reactions can be conducted in one vessel, albeit with some sacrifice in overall yield.

The present process may be better understood with reference to the Drawing in which like reference numerals are used to indicate like elements.

Suitable apparatus for practicing the present invention includes a multi-tray, glass Oldershaw column 10, enclosed in a cooling jacket 12. The apparatus also includes a bottom receiver 14, feed pump 16, and recycle pump 18. The initial feed material 20 consists of solvent (not specifically shown), cycloalkene (not specifically shown), and catalyst (not specifically shown). Pump 16 charges the initial feed material 20 into the top of column 10. The temperature of the cooling jacket 12 on column 10 can be adjusted to between 40 and 60 degrees C. using flowing water 32, 32'. Recycle pump 18 can be used to establish a recycle flow 22 in column 10. A carrier gas 26 consisting of a predetermined percentage of oxygen in carbon dioxide can be fed to ozone generator 24. The gas 28 exiting the ozone generator 24 can be measured to determine the percentage of ozone. A pressure relief valve 36 can be used to control the pressure of gas 28. Additional cycloalkene solution can be fed to the top of the column 10. The balance between the ozone and the cycloalkene feed should allow for an excess of ozone in the reactor off-gas 30 at all times. Pump 34 is used to pump dicarboxylic acid product to additional apparatus (not shown) or storage.

The primary reactant used in this invention is a cycloalkene having 6 to 12 carbon atoms. Cyclohexene is a preferred reactant because the principal product is adipic acid, which has wide uses, particularly in making 6,6 nylon. Cyclododecene is also a preferred reactant because the principal product is dodecandioic acid, which can be used as an intermediate to make 6,12 nylon or as a cross-linker in spray coatings, among other things.

The solvent used in this invention can be a mono- or dicarboxylic acid or a mono- or di-alcohol containing 1 to 9 carbon atoms. Solvents which do not actively participate in the ozonolysis reaction should not be used. Preferred solvents are formic acid, acetic acid, and propionic acid.

A wide variety of Bronsted and Lewis bases are suitable as base catalysts, because they will catalyze the re-arrangement reaction. For example, primary amines, secondary amines, tertiary amines, pyridines, picolines, and pyrroles, are suitable. Because the base catalyst does not necessarily need to be soluble in the reaction solution, basic polymeric resins may be used. Preferred base catalysts are Group I metal salts of the acid solvent. For example when propionic acid is used as the solvent, sodium propionate is a preferred base catalyst. However, any soluble metal salt of any low molecular weight carboxylic acid would be suitable.

This invention involves contacting the liquid reaction mixture with a gas that contains both oxygen and ozone. The contacting step can take place in any suitable gas/liquid reactor. Any reactor which contacts the liquid and gas and which affords good mass transfer between the gas and the liquid can be used. One preferred reactor is an Oldershaw column, designed originally for distillation. A liquid circulating loop with an inline mixer to facilitate gas/liquid contact would also be suitable.

After the contacting of the reaction mixture with the oxygen and ozone-containing gas is complete, the resulting product mixture is slowly cooled and the dicarboxylic acid is re-crystallized from the solvent solution. The crystals are filtered, washed with a small quantity of cold solvent and dried in a vacuum oven. A small quantity of the crystals can be dissolved in solvent with an internal standard, converted to the silyl ester with bis(trimethylsilyl)trifluoroacetamide (BSTFA) or similar agent, and then analyzed by gas chromatography. In this way, product purity can be determined. Purity in the range of 85 to 95% is preferred.

It is possible that not all the intermediates resulting from the reaction will be fully converted into the dicarboxylic acid after a reasonable period of reaction time. As a result, the mother liquor remaining after the dicarboxylic acid is crystallized out of the product mixture can be re-used as the solvent in another pass through the reactor. By reusing the mother liquor in this manner, the maximum process yield is obtained.

The invention is illustrated by the following, nonlimiting examples.

EXAMPLES

Example 1

A reactor system consisting of a jacketed 1 inch, 10 tray glass Oldershaw column, 250 cc bottom receiver, feed pump, and recycle pump were assembled. The initial feed material consisted of 236.25 g. of propionic acid solvent, 12.5 g. of cyclododecene, and 1.25 g. of sodium propionate catalyst. 120 g. of the initial feed material were charged into the reactor system. The temperature of the jacket on the Oldershaw column was adjusted to 50° C. and a recycle flow of 50 cc/min. was established using the recycle pump. A ClearWater Tech modelM-1500 ozone generator was attached to the system. A carrier gas consisting of 20% oxygen in carbon dioxide was fed to the reactor at 2000 cc/min. The gas exit the ozone generator was measured to contain 0.80% ozone. After approximately 1 hour of feeding ozone, the ozone level was shown to increase as indicated by a gas bubbler containing aqueous potassium iodide. At that point, the additional 130 g. of cyclododecene solution was fed to the top of the column at a rate of 1 cc/min. The balance between the ozone and the cyclododecene fed allowed an excess of ozone in the reactor off gas at all times. When the additional feed material was depleted, the ozone was fed for another 30 minutes. The reactor solution was removed from the reactor and slowly cooled to room temperature over night. Solid dodecanedioic acid crystallized from solution and was filtered. The crystals were dried and analyzed.

The mother liquor from the crystallization was mixed with another batch of 12.5 g. of cyclododecene and 1.25 g. of sodium propionate. Enough propionic acid was added to the mixture to make a final weight of 250 g. This new feed was again reacted as above. This process was repeated for a total of seven passes through the reactor. The results of this series of reactions are given in Table I. The average dry dodecanedioc acid (DDDA) yield for the fourth, fifth, sixth and seventh passes is 78.8% based on the weight of cyclododecene fed.

TABLE I

Results Of Recycle Experiments

| Pass | Crystal Purity Percent DDDA | DDDA In-Hand Yield-Percent |
|---|---|---|
| 1 | — | 0 |
| 2 | 93.6 | 96.7 |
| 3 | 91.2 | 49.0 |
| 4 | 92.9 | 82.8 |
| 5 | 88.7 | 62.3 |
| 6 | 89.8 | 73.8 |
| 7 | 85.4 | 96.4 |
| Avg for Passes 4, 5, 6, 7 | 88.0 | 78.8 |

Example 2

A reactor system as described in example 1 was assembled. The initial feed material consisted of 236.25 g. of propionic acid solvent, 12.5 g. of cyclododecene, and 1.25 g. of sodium propionate catalyst. 120 g. of the initial feed material were charged into the reactor system. The temperature of the jacket on the Oldershaw column was adjusted to 50° C. and a recycle flow of 50 cc/min. was established using the recycle pump. A ClearWater Tech model M-1500 ozone generator was attached to the system. A carrier gas consisting of 20% oxygen in carbon dioxide was fed to the reactor at 2000 cc/min. The gas exit the ozone generator was measured to contain 0.80% ozone. After approximately 1 hour of feeding ozone, the ozone level was shown to increase as indicated by a gas bubbler containing aqueous potassium iodide. At that point, the additional 130 g. of cyclododecene solution was fed to the middle of the column at a rate of 0.75 cc/min. The balance between the ozone and the cyclododecene fed allowed an excess of ozone in the reactor off gas at all times. When the additional feed material was depleted, the ozone was fed for another 30 minutes. The reactor solution was removed from the reactor and slowly cooled to room temperature over night. Solid dodecanedioic acid crystallized from solution and filtered. The crystals were dried and analyzed.

The mother liquor from the crystallization was mixed with another batch of 12.5 g. of cyclododecene and 1.25 g. of sodium propionate. Enough propionic acid was added to the mixture to make a final weight of 250 g. This new feed was again reacted as above. This process was repeated for a total of seven passes through the reactor. The results of this series of reactions are given in Table I. The average dry DDDA yield for the fourth, fifth, sixth and seventh passes is 72.3% based on the weight of cyclododecene fed.

TABLE II

Results of Recycle Experiments

| Pass | Crystal Purity Percent DDDA | DDDA In-Hand Yield-Percent |
|---|---|---|
| 1 | — | 0.00 |
| 2 | 97.1 | 92.19 |
| 3 | 93.0 | 63.20 |
| 4 | 93.2 | 68.10 |
| 5 | 90.6 | 66.71 |
| 6 | 93.4 | 85.53 |
| 7 | 92.9 | 68.99 |
| Avg for Passes 4, 5, 6, 7 | 92.5 | 72.3 |

Example 3

A reactor system consisting of a jacketed 1 inch, 10 tray glass Oldershaw column, 250 cc bottom receiver, feed pump, and recycle pump were assembled. The initial feed material consisted of 223.75 g. of propionic acid solvent, 25 g. of cyclohexene, and 1.25 g. of sodium propionate catalyst. 120 g. of the initial feed material were charged into the reactor system. The temperature of the jacket on the Oldershaw column was adjusted to 50° C. and a recycle flow of 50 cc/min. was established using the recycle pump. A ClearWater Tech modelM-1500 ozone generator was attached to the system. A carrier gas consisting of 8% oxygen in carbon dioxide was fed to the reactor at 2000 cc/min. The gas exit the ozone generator was measured to contain 0.80% ozone. After approximately 1 hour of feeding ozone, the ozone level was shown to increase as indicated by a gas bubbler containing aqueous potassium iodide. At that point, the additional 130 g. of cyclohexene solution was fed to the top of the column at a rate of 1 cc/min. The balance between the ozone and the cyclododecene fed allowed an excess of ozone in the reactor off gas at all times. When the additional feed material was depleted, the ozone was fed for another 30 minutes. The reactor solution was removed from the reactor and slowly cooled to room temperature over night. Solid adipic acid crystallized from solution and was filtered. The crystals were dried and analyzed.

The mother liquor from the crystallization was mixed with another batch of 12.5 g. of cyclododecene and 1.25 g. of sodium propionate. Enough propionic acid was added to the mixture to make a final weight of 250 g. This new feed was again reacted as above. This process was repeated for a total of seven passes through the reactor. The results of this series of reactions are given in Table II. The average dry adipic acid yield for the fifth, sixth and seventh passes is 28.1% based on the weight of cyclohexene fed.

TABLE III

Results of Single Reactor Recycle with Cyclohexene

| Pass | Crystal Purity Percent Adipic Acid | Calculated Yield-Percent |
|---|---|---|
| 1 | — | — |
| 2 | — | — |
| 3 | 97.2 | 19.7 |
| 4 | 97.2 | 12.4 |
| 5 | 92.5 | 46.0 |
| 6 | 86.8 | 10.5 |
| 7 | 89.8 | 27.8 |
| Avg for Passes 5, 6, 7 | 89.7 | 28.1 |

What is claimed is:

1. A process for making an alkanedioc acid, in which the alkane moiety contains 6 to 12 carbon atoms, comprising:

forming a reaction mixture comprising a cycloalkene having the same number of carbon atoms as the alkane moiety of the alkanedioc acid, a $C_1$ to $C_9$ organic acid, and a metal salt of the organic acid, and contacting the mixture simultaneously with oxygen and ozone at a temperature between about 40 to about 60 degrees C. to obtain a product mixture.

2. The process of claim 1 further comprising crystallizing the alkanedioc acid from the product mixture.

3. The process of claim 2 in which the metal salt of the organic acid is a sodium salt.

4. The process of claim 3 in which the sodium alkanate is sodium propionate.

5. The process of claim 4 in which the solvent is an alkanoic acid.

6. The process of claim 5 in which the alkanoic acid is propionic acid.

7. The process of claim 6 in which the temperature is 50 degrees C.

8. The process of claim 7 in which the cycloalkene is cyclododecene.

9. The process of claim 7 in which the cycloalkene is cyclohexene.

* * * * *